United States Patent
Cho et al.

(10) Patent No.: US 11,213,464 B2
(45) Date of Patent: Jan. 4, 2022

(54) SOLID TEMPORAL COLORIMETRIC HYDROGEL COSMETIC COMPOSITION HAVING FLEXIBILITY BY GAMMA-RAY IRRADIATION

(71) Applicant: COSMECCA KOREA Co., Ltd., Chungcheongbuk-do (KR)

(72) Inventors: Hyun Dae Cho, Chungcheongbuk-do (KR); Jae Yong Seo, Chungcheongbuk-do (KR); Ju Tae Jeong, Chungcheongbuk-do (KR); Soon Ho Choi, Gyeonggi-do (KR); Jung Won Shin, Gyeonggi-do (KR)

(73) Assignee: COSMECCA KOREA CO., LTD., Chungcheongbuk-Do (KR)

( * ) Notice: Subject to any disclaimer, the term of this patent is extended or adjusted under 35 U.S.C. 154(b) by 0 days.

(21) Appl. No.: 16/496,477

(22) PCT Filed: Mar. 12, 2019

(86) PCT No.: PCT/KR2019/002841
§ 371 (c)(1),
(2) Date: Sep. 23, 2019

(87) PCT Pub. No.: WO2019/177336
PCT Pub. Date: Sep. 19, 2019

(65) Prior Publication Data
US 2020/0306150 A1 Oct. 1, 2020

(30) Foreign Application Priority Data
Mar. 12, 2018 (KR) ........................ 10-2018-0028816

(51) Int. Cl.
| | |
|---|---|
| *A61K 8/06* | (2006.01) |
| *A61K 8/04* | (2006.01) |
| *A61K 8/34* | (2006.01) |
| *A61K 8/36* | (2006.01) |
| *A61K 8/60* | (2006.01) |
| *A61K 8/73* | (2006.01) |
| *A61K 8/81* | (2006.01) |
| *A61K 8/86* | (2006.01) |
| *A61K 8/89* | (2006.01) |
| *A61K 8/92* | (2006.01) |
| *A61Q 1/02* | (2006.01) |
| *A61K 8/891* | (2006.01) |

(52) U.S. Cl.
CPC .............. *A61K 8/062* (2013.01); *A61K 8/042* (2013.01); *A61K 8/345* (2013.01); *A61K 8/361* (2013.01); *A61K 8/60* (2013.01); *A61K 8/735* (2013.01); *A61K 8/8176* (2013.01); *A61K 8/86* (2013.01); *A61K 8/891* (2013.01); *A61K 8/92* (2013.01); *A61Q 1/02* (2013.01); *A61K 2800/42* (2013.01)

(58) Field of Classification Search
CPC .......... A61K 8/86; A61K 8/8176; A61K 8/60; A61K 8/062; A61K 8/361; A61K 8/29; A61K 8/345; A61K 8/73; A61K 8/92; A61Q 19/00
See application file for complete search history.

(56) References Cited

U.S. PATENT DOCUMENTS

2015/0305990 A1   10/2015   Yoo et al.

OTHER PUBLICATIONS

International Search Report dated Jun. 24, 2019, in PCT/KR2019/002841.
Written Opinion dated Jun. 24, 2019, in PCT/KR2019/002841.

*Primary Examiner* — Zohreh A Fay
(74) *Attorney, Agent, or Firm* — Bacon & Thomas, PLLC

(57) ABSTRACT

A solid temporal colorimetric hydrogel cosmetic composition includes 15 to 99.90 wt % of the water phase part and 0.10 to 85 wt % of the oil phase part, having a refractive index difference of 0 to 0.02 therebetween, and having a color change according to variations in a refractive index difference between the water phase part and the oil phase difference when applied to the skin. The cosmetic composition not only has flexibility through irradiation of gamma-rays, but also enables an optimal application time of the cosmetic composition to be visually confirmed through a color change from transparency to ivory white due to a change in the refractive index difference caused by absorbency and volatilization of water when applying the composition to the skin. The cosmetic composition is capable of improving quality of a product although a preservative irritating to the skin is not added.

14 Claims, No Drawings

SOLID TEMPORAL COLORIMETRIC HYDROGEL COSMETIC COMPOSITION HAVING FLEXIBILITY BY GAMMA-RAY IRRADIATION

FIELD OF THE INVENTION

The present invention relates to an oil-in-water type solid hydrogel cosmetic composition having flexibility by irradiation of gamma-rays and, more particularly, to a cosmetic composition enabling an optimal application time of the cosmetic composition to be visually confirmed through a color change from transparency to ivory white according to a change in the refractive index difference due to absorbency and volatilization of water when applying the composition to the skin using a refractive index difference between a water phase part and an oil phase part within the composition.

BACKGROUND OF THE INVENTION

Products using color changing materials have recently been released in a large amount by reflecting needs of customers, and have typically been used in various industrial fields such as a fiber (mask) which reacts with temperature of the skin to inform of symptoms of cold and others, a container which informs of an optimal digestion temperature of food, money security uses, etc.

Many researches have been conducted on such materials using color change, the researches including a method of performing a synthesis process by adding transition elements as a dopant, a method of exhibiting a color by absorbing a wavelength in a specific visible ray range as a conjugation compound by connection of the polymers according to a temperature change in diacetylene-based polymers, a method of using pH variations of the materials, etc.

However, since these existing materials are immediately reacted by temperature, pH and the like of the skin, the existing materials are not suitable for a mask pack which is required to be used on the skin for a predetermined time. Further, since the existing materials mostly contain harmful metals or the conjugation compound, it is difficult to secure safety due to elution, and there is a problem in price competitiveness or mass production when the existing materials are used as materials for cosmetics.

Further, although a hydrogel has been used so far mainly for the purpose of a bio drug delivery system, skin wound healing and others, there has recently been a tendency to develop a hydrogel that is applied to cosmetics. A hydrophilic polymer is mostly used as the hydrogel to facilitate skin penetration of the hydrogel. The hydrophilic polymer is mainly developed in accordance with the form of a product by appropriately mixing a branched gelated polymer, an electrolytic type gelated polymer and others, and the hydrophilic polymer as a hydrogel with high affinity can easily and promptly carry out drug delivery to the skin.

However, although a hydrogel cosmetic composition used in existing cosmetics is characterized in that the hydrogel cosmetic composition is prepared by using natural polymers including agar, carrageenan, glucomannan, galactomannan, algin and others, physical properties of the natural polymers are changed according to states or production conditions of the natural polymers, and a phenomenon that water comes out of the solid type gel over time occurs in a solid type gel prepared using the natural polymers due to characteristics of the natural polymers. Therefore, there is a problem that quality standards of the solid type gel cannot be determined.

Further, existing all mask packs have a problem of causing skin irritation since a large amount of preservative harmful to the skin is used in the mask packs to prevent microbial contamination.

Accordingly, it is required to develop a color changing mask pack cosmetic material of an indicator concept which enables an optimal application time to be visually confirmed according to skin conditions of a user, temperature and moisture extents of the skin of the user, and others during using as a visual confirming method as well as efficacy according to skin penetration, and there is a need to stably produce such a cosmetic material, improve quality of the cosmetic material such as stability of physical properties, and improve a skin irritation problem caused by the preservative.

Prior Art Documents (Patent document 1) Korean Patent Publication No. 10-2010-0082742
(Patent document 2) Korean Patent Publication No. 10-2010-0039776
(Patent document 3) Korean Patent Publication No. 10-2011-0075622
(Patent document 4) Korean Patent Registration No. 10-1172987
(Patent document 5) Korean Patent Publication No. 10-2017-0012812

SUMMARY OF THE INVENTION

The present invention has been devised to solve the aforementioned problems, and a first objective of the present invention is to provide a solid temporal colorimetric hydrogel cosmetic composition having flexibility by irradiation of gamma-rays, the hydrogel cosmetic composition enabling an optimal application time of the cosmetic composition to be visually confirmed through a color change from transparency to ivory white according to a change in the refractive index difference due to absorbency and volatilization of water when applying the composition to the skin using a refractive index difference between a water phase part and an oil phase part within the composition having flexibility through irradiation of gamma-rays.

Furthermore, a second objective of the present invention is to provide a cosmetic composition which inhibits microbial proliferation of a cosmetic material through irradiation of gamma-rays such that the cosmetic composition is capable of improving quality of a product although a preservative irritating to the skin is not added.

To achieve the objectives, a hydrogel cosmetic composition according to the present invention uses gamma-rays for the purpose of forming a solid gel having flexibility through crosslinking of polymer even without addition of a crosslinking agent and performing a sterilization process for preventing addition of the preservative.

In the present invention, gamma-rays used in gamma-ray irradiation may be used in an irradiation dose of 5 to 50 kGy, preferably 10 to 30 kGy. It is difficult to form a solid gel since a cross-linkage is not formed when the gamma-rays are used in an irradiation dose of less than 5 kGy, and the solid gel may be easily broken since flexibility of the solid gel is decreased although strength of the solid gel is increased when the gamma-rays are used in an irradiation dose of more than 50 kGy.

Here, a solid type hydrogel having flexibility formed by crosslinking a polymer having reactive groups through irradiation of gamma-rays may maintain certain physical properties, and proliferation of microorganisms in the cosmetic material is inhibited by a sterilization function of the gamma-rays. Therefore, the solid type hydrogel may help in solving a skin irritation problem due to the preservative and improving quality of the product.

Although only the gamma-rays as radiation to be irradiated has been described in the present invention, it is clear that the radiation is not limited to the gamma-rays, and radiation such as ultraviolet rays or electron rays can also be applied.

Furthermore, a color change from transparency to ivory white according to a skin wearing time of the cosmetic material can be made by varying a refractive index difference of a water phase part or an oil phase part when applying a cosmetic material in an emulsion type formulation to the skin.

Namely, a color change over time of a solid hydrogel cosmetic material according to the present invention allows a water phase part and an oil phase part having the same refractive index or different refractive indexes to be formed, and changes a refractive index difference between the water phase part and the oil phase part by absorbency and volatilization of water when the cosmetic material is applied to the skin, thereby enabling a color change from transparency to ivory white such that an optimal application time of the cosmetic material can be visually confirmed accordingly.

This uses a phenomenon that visible light is scattered to be seen as ivory white when emulsion particles have a size of 100 nm or more and a recent research that a transparent emulsion form can be realized by reducing a refractive index difference between the oil phase part and the water phase part in an emulsion type formulation.

Furthermore, in order to prepare a solid hydrogel cosmetic composition of the present invention, an oil-in-water type emulsion including the water phase part and the oil phase part should be first formed.

At this time, the refractive index difference between the water phase part and the oil phase part at 25° C. is 0 to 0.02, preferably 0 to 0.01, and more preferably 0 to 0.005. It is difficult to expect discoloration from transparency to ivory white since the refractive index difference is large when the refractive index difference is more than 0.02.

Furthermore, a solid hydrogel cosmetic composition of the present invention may comprise 15 to 99.90 wt %, preferably 20 to 90 wt % of the water phase part based on the total weight percentage of the composition. It is difficult to form an oil-in-water type emulsion when the composition comprises less than 15 wt % of the water phase part while it is difficult to realize an opaque ivory white emulsion when the composition comprises more than 99.90 wt % of the water phase part. Further, a solid hydrogel cosmetic composition of the present invention may comprise 0.10 to 85 wt %, preferably 10 to 80 wt % of the oil phase part based on the total weight percentage of the composition. It is difficult to realize an opaque ivory white color since the composition comprises a small amount of the oil phase part when the composition comprises less than 0.10 wt % of the oil phase part while formulation stability may be deteriorated when the composition comprises more than 85 wt % of the oil phase part.

In a solid hydrogel cosmetic composition of the present invention, the water phase part may include a polymer, a refractive index regulator, purified water, etc.

At this time, the water phase part comprises 3.0 to 30 wt %, preferably 7.0 to 15 wt % of the polymer based on the total weight percentage of the water phase part. It is difficult to perform a gelation process when the water phase part comprises less than 3.0 wt % of the polymer based on the total weight percentage of the water phase part while it is difficult to dissolve the polymer in the water phase part when the water phase part comprises more than 30 wt % of the polymer based on the total weight percentage of the water phase part.

Furthermore, the water phase part comprises 3 to 60 wt %, preferably 20 to 50 wt % of the refractive index regulator based on the total weight percentage of the water phase part.

The refractive index regulator obstructs gelation by causing competitive inhibition with the polymer when the water phase part comprises more than 60 wt % of the refractive index regulator based on the total weight percentage of the water phase part. An emulsion with ivory white is formed, and it is not possible to observe discoloration from transparency to ivory white from the emulsion resultingly since a regulation effect of increasing refractive index of the water phase part is less such that the refractive index difference between the water phase part and the oil phase part becomes larger when the water phase part comprises less than 3 wt % of the refractive index regulator based on the total weight percentage of the water phase part.

Here, examples of the polymer may include a zwitterionic polymer, a cationic polymer, an anionic polymer, and any polymer as a nonionic polymer comprising reactive groups in the form of alcohol, a carboxyl group, an amine group, ether, sulfonic acid, ketone, etc. A solid cosmetic material having flexibility can be produced by dispersing the polymer in an aqueous solution and irradiating gamma-rays to the polymer dispersed in the aqueous solution, thereby forming a cross-linkage.

Examples of the zwitterionic polymer include zwitterionic starches, dimethyl diallyl ammonium chloride derivatives (e.g., acrylamide-acrylic acid-dimethyl diallyl ammonium chloride copolymer), methacrylic acid derivatives (e.g., poly methacryloyl ethyl dimethyl betaine, N-methacryloyl oxyethyl N,N-dimethyl ammonium-α-N-methyl carboxy betaine/alkyl methacrylate copolymer, etc.).

Examples of the cationic polymer include quaternary ammonium polysaccharides (e.g., cationic cellulose, cationic hydroxyethyl cellulose, cationic guar gum, cationic locust bean gum, cationic starches, etc.), dimethyl diallyl ammonium chloride derivatives (e.g., dimethyl diallyl ammonium chloride/acrylamide copolymer, etc.), vinylpyrrolidone derivatives (e.g., vinyl pyrrolidone/methacrylamide propyl trimethyl ammonium copolymer, vinyl pyrrolidone/methyl vinyl imidazolium chloride copolymer, etc.), methacrylic acid derivatives (e.g., methacryloyl ethyl dimethyl betaine/methacryloyl ethyl trimethyl ammonium chloride-2-hydroxyethylmethacrylate copolymer, etc.), etc.

Examples of the anionic polymer include polyacrylic acid and its salts, polymethacrylic acid and its salts, hyaluronic acid and its salts, acetylated hyaluronic acid and its salts, aliphatic carboxylic acid and its salts (e.g., methyl vinyl ether/maleic acid copolymer, carboxyvinyl polymer, etc.), polyacrylic acid containing a polyvalent allyl ether as a crosslinking agent and its salts, etc.

Examples of the nonionic polymer include polyvinylpyrrolidone, polyethylene glycol, polyethylene glycol/polypropylene glycol copolymer, polyethylene glycol/polypropylene glycol/polybutylene glycol copolymer, vinyl pyrrolidone/vinyl acetate copolymer, vinyl pyrrolidone/dimethylaminoethylmethacrylate copolymer, vinyl caprolactam/vinylpyrrolidone/dimethylaminoethyl methacrylate copolymer, cellulose and its derivatives (e.g., methyl cellulose, ethyl cellulose, hydroxyethyl cellulose, hydroxypropyl cellulose, etc.), keratin and collagen, and their derivatives, algin and its salts, pullulan, agar, gelatin, tarmarind seed polysaccharide, xanthan gum, carrageenan, galactomannan, glucomannan, pectin, guar gum, gum Arabic, crystalline cellulose, alginic acid, albumin, casein, gellan gum, dextrin, chitosan and its derivatives, starch, etc.

Although the polymer may include one or more selected from the group including above-mentioned hydrophilic gelation agents, the polymer is not limited thereto, and hyaluronic acid and its salts, polyvinyl alcohol, polyvinyl pyrrolidone, and carrageenan which have high reactivities by containing a large number of functional groups such as a carboxyl group, a hydroxyl group, an amine group, a sulfonic acid group and others are particularly suitable as the polymer.

Furthermore, any ordinary water-soluble cosmetic material ingredients may be used as the refractive index regulator, and examples of the refractive index regulator may include at least one selected from high polarity materials such as polyhydric alcohols (e.g., ethylene glycol, glycerin, propylene glycol, butylene glycol, pentylene glycol, hexylene glycol, diglycerol, polyglycerol, etc.), saccharide (e.g., sorbitol, maltitol, sucrose, lactitol, xylitol, etc.), polyoxyalkylene, polyoxyalkylene copolymer (e.g., polyethylene glycol, polyethylene glycol/polypropylene glycol copolymer, etc.), polyoxyalkylene-containing alcohols (polyoxyethylene-glycerol ether, etc.), silicone/polyalkylene copolymer (dipolyoxy ethyleneoxy dimethyl silane, etc.), etc.

Furthermore, in a solid hydrogel cosmetic composition of the present invention, the water phase part and the oil phase part may include a surfactant. At this time, it goes without saying that a surfactant for performing an emulsification process may be contained in a dissolution-facilitating portion of the water phase part or the oil phase part.

At this time, the solid hydrogel cosmetic composition comprises 0.05 to 30 wt %, preferably 0.5 to 20 wt % of the surfactant based on the total weight percentage of the composition. It is difficult to form an emulsion when the composition comprises less than 0.05 wt % of the surfactant based on the total weight percentage of the composition while the surfactant is not suitable for a color change of the present invention since emulsion particles are decreased compared to ¼ of a wavelength of visible rays such that the emulsion particles are shown in a transparent form when the composition comprises more than 30 wt % of the surfactant based on the total weight percentage of the composition.

Here, an emulsion can be acquired by using an anionic surfactant, a cationic surfactant, a nonionic surfactant and an amphoteric surfactant as the surfactant.

Examples of the anionic surfactant may include fatty acid and its salts (e.g., sodium laurate, sodium stearate, potassium oleate, etc.), alkyl sulfuric acid and its salts, alkylbenzene sulfonic acid (e.g., hexylbenzene sulfonic acid, octylbenzene sulfonic acid, dodecylbenzene sulfonic acid, etc.) and its salts, polyoxyalkylene alkyl ether sulfonic acid and its salts, polyoxyethylene alkyl ether sulfuric ester and its salts, sulfosuccinic acid alkyl ester and its salts, polyoxyalkylene alkyl phenyl ether sulfuric acid and its salts, polyoxyalkylene alkyl ether acetic acid and its salts, alkyl phosphoric acid and its salts, polyoxyalkylene alkyl ether phosphoric acid and its salts, acyl glutamic acid and its salts, acyl sulfonic acid and its salts, alkyl sulfonic acid and its salts, alkylamide phosphoric acid and its salts, alkyloyl alkyl taurine and its salts, acylamino acid and its salts, etc.

Examples of the cationic surfactant may include alkyl trimethyl ammonium chloride or bromide (e.g., stearyl trimethyl ammonium chloride, lauryl trimethyl ammonium chloride, cetyl trimethyl ammonium chloride, stearyl trimethyl ammonium bromide, lauryl trimethyl ammonium bromide, etc.), dialkyl dimethyl ammonium chloride or bromide (e.g., distearyl dimethyl ammonium chloride, distearyl dimethyl ammonium bromide, dicoco dimethyl ammonium chloride, etc.), benzalkonium chloride, alkyl benzalkonium chloride, benzethonium chloride, diethyl aminoethyl amide stearate, dimethyl aminopropyl amide stearate, alkyl pyridinium chloride, etc.

Examples of the nonionic surfactant may include polyoxyalkylene alkyl ether (e.g., polyoxyethylene stearyl ether, polyoxyethylene cetyl ether, etc.), polyoxyalkylene fatty acid esters (e.g., polyoxyethylene stearate, polyoxyethylene laurate, polyoxyethylene behenate, etc.), polyoxyalkylene castor oil, polyoxyalkylene alkyl phenol ether, sorbitan fatty acid ester (sorbitan stearate), polyoxyalkylene sorbitan alkyl ester (e.g., polyethylene glycol (20) sorbitan stearate), polyoxyalkylene glycerol fatty acid ester, polyglycerol alkyl ether, polyglycerol fatty acid ester, sucrose fatty acid ester, fatty acid alkyl amide, alkyl glucoside, polyoxyalkylene-linked silicone, polyglycerol-linked silicone, polyoxyethylene/polyoxypropylene copolymer, etc.

Examples of the amphoteric surfactant may include imidazoline type amphoteric surfactants (e.g., sodium 2-undecyl-N,N,N-(hydroxyethylcarboxymethyl)-2-imidazoline, 2-cocoyl-2-imidazoliniumhydroxide-1-carboxyethyloxy-2-sodium salt, etc.), amidobetaine type amphoteric surfactants, alkylbetaine type amphoteric surfactants (e.g., lauryl dimethyl aminoacetic acid betaine, myristyl betaine, etc.), alkyl amidobetaine type amphoteric surfactants, alkyl sulfobetaine type amphoteric surfactants, amidosulfobetaine type amphoteric surfactants, hydroxy sulfobetaine type amphoteric surfactants, carbobetaine type amphoteric surfactants, aminocarboxylic betaine type amphoteric surfactants, etc.

Although examples of the surfactant may include one or more surfactants selected from the above-mentioned surfactant groups, the surfactant is not limited thereto. Preferably, it is appropriate that the examples of the surfactant include nonionic surfactants that are less irritating.

Furthermore, in a solid hydrogel cosmetic composition of the present invention, the oil phase part may include a refractive index regulator and oil.

The oil of the oil phase part comprises oily ingredients including a silicon-based oil, a hydrocarbon oil, an ester-based oil, a natural oil, a higher alcohol, a fatty acid, etc.

The silicon-based oil is classified into volatile silicon oil and non-volatile silicon oil, examples of the non-volatile silicon oil may include polydimethylsiloxane (dimethicone, viscosity of 5 to 1,000,000 cst) capped by linear trimethylsiloxane, alkyl chain-linked polysiloxane, methylphenylsiloxane, etc., examples of the volatile silicon oil may include a linear volatile siloxane (I), a ring-shaped volatile siloxane (II) with a low molecular weight, a branched volatile siloxane (III) with a low molecular weight, etc., examples of the linear volatile siloxane (I) may include hexamethyldisiloxane (MM), octamethyltrisiloxane (MDM), decamethyltetrasiloxane (MD2M), dodecamethylpentasiloxane (MD3M), tetramethylhexasiloxane (MD4M), hexadecamethylheptasiloxane (MDSM), etc., examples of the ring-shaped volatile siloxane (II) may include hexamethylcyclotrisiloxane (D3), octamethylcyclotetrasiloxane (D4), decamethylcyclopentasiloxane (D5) and dodecamethylcyclohexasiloxane (D6), and examples of the branched volatile siloxane (III) may include heptamethyl-3-((trimethylsilyl)oxy)trisiloxane (M3T), hexamethyl-3,3-bis((trimethylsilyl)oxy)trisiloxane (M4T), etc.

Examples of the hydrocarbon oil may include liquid paraffin, liquid isoparaffin, Vaseline, isododecane, isohexadecane, polyisobutylene, polybutene, ozokerite, ceresin, microcrystalline wax, paraffin wax, polyethylene, polypropylene, squalane, polydecene, etc.

Examples of the ester-based oil may include isopropyl myristate, ethyl laurate, ethyl myristate, isopropyl palmitate, butyl laurate, hexyl laurate, caprylic/capric triglyceride, isopropyl myristate, triethylhexanoin, cetyl ethylhexanoate, tristearin, etc.

Examples of the natural oil may include animal oil, vegetable oil, avocado oil, linseed oil, candellila wax, horse oil, sunflower oil, castor oil, coconut oil, rice bran oil, almond oil, soybean oil, kernel oil, beeswax, coconut butter, lanolin, etc.

Examples of the higher alcohol may include lauryl alcohol, myristyl alcohol, palmityl alcohol, stearyl alcohol, oleyl alcohol, hexadecyl alcohol, isostearyl alcohol, hexadodecanol, octyldodecanol, cholesterol, sitosterol, etc.

Examples of the fatty acid may include lauric acid, myristic acid, palmitic acid, stearic acid, oleic acid, linoleic acid, linolenic acid, arachidonic acid, eicosapentaenoic acid, docosahexaenoic acid, isostearic acid, hydroxystearic acid, etc.

Although examples of the oil of the oil phase part may include one or more oils selected from the above-mentioned oil groups, the oil is not limited thereto. Preferably, it is appropriate that the examples of the oil include liquid oils.

The refractive index regulator of the oil phase part may comprise all ingredients composing the oil phase part by including oil. In general, a refractive index regulator with a low molecular weight has a low refractive index while a refractive index regulator with a high molecular weight has a high refractive index. Further, a refractive index regulator comprising a silicon-based oil has a remarkably low refractive index compared to a refractive index regulator comprising hydrocarbon oil, and refractive index can be regulated by combining a low refractive index oil with a high refractive index oil.

Refractive index of the oil phase part is regulated by the following numerical formula 1.

$$RI_{mix} = [\Sigma(W_i \times n_i)]/\Sigma W_i \qquad \text{[Numerical Formula 1]}$$

($RI_{mix}$: refractive index of a mixed oil, $W_i$: weight of each of used oils, $n_i$: refractive index of each of the used oils)

Furthermore, a solid hydrogel cosmetic material according to the present invention can be acquired using a general production method of an oil-in-water type cosmetic material, a specific production method is as follows.

(1) A Step of Mixing and Dissolving Respective Ingredients of the Water Phase Part After weighing fixed quantities of the respective ingredients of the water phase part, the weighed fixed quantities of the respective ingredients of the water phase part are mixed and dissolved using Agi mixer at 60 to 85° C., preferably at 80° C. and 4,000 rpm for 50 to 70 minutes, and preferably for 60 minutes.

(2) A Step of Mixing and Dissolving Respective Ingredients of the Oil Phase Part After weighing fixed quantities of the respective ingredients of the oil phase part, the weighed fixed quantities of the respective ingredients of the oil phase part are mixed and dissolved.

(3) A Step of Forming an Emulsion by Emulsifying a Mixed and Dissolved Water Phase Part into a Mixed and Dissolved Oil Phase Part After slowly injecting the mixed and dissolved oil phase part into the mixed and dissolved water phase part, an emulsification process is performed using Homo mixer at 60 to 85° C., preferably at 80° C. and 4,000 rpm for 8 to 20 minutes, and preferably for 10 minutes.

(4) A Step of Irradiating the Gamma-Rays to the Emulsion

After injecting the emulsion into a container, the gamma-rays are irradiated to the emulsion with irradiation dose differences of 5 kGy, 15 kGy, 35 kGy and 50 kGy within an irradiation dose range of 5 to 50 kGy.

(5) A Step of Confirming Whether a Solid Gel Having Fluidity is Formed or not

A final composition is obtained through such a preparation process.

A solid hydrogel cosmetic composition according to the present invention may additionally include, except for the above-mentioned ingredients, materials usable in cosmetics such as a whitening agent, a wrinkle alleviating agent, an antioxidant, an anti-inflammatory agent, perfume, coloring matter, a germicide, a pH adjusting agent, a use feeling enhancer, an oxidation stabilizer and others within a range of preventing effects of the composition from being lowered.

A hydrogel cosmetic composition according to the present invention has effects that the cosmetic composition not only has flexibility through irradiation of gamma-rays, but also enables an optimal application time of the cosmetic composition to be visually confirmed through a color change from transparency to ivory white due to a change in the refractive index difference caused by absorbency and volatilization of water when applying the composition to the skin using a refractive index difference between a water phase part and an oil phase part within the composition.

Furthermore, a hydrogel cosmetic composition according to the present invention has an effect that the cosmetic composition is capable of improving quality of a product although a preservative irritating to the skin is not added by inhibiting microbial proliferation of a cosmetic material through irradiation of gamma-rays.

DETAILED DESCRIPTION OF THE INVENTION

Hereinafter, the present invention will be described in more detail with reference to the following Examples and Comparative Examples. However, the following Examples and Comparative Examples are provided for illustrative purposes only, and the scope of the present invention should not be limited thereto in any manner. Further, the description about usual measurement experiments in a test process of measuring efficacy has been omitted.

<Example 1> Confirming Oil-in-Water Type Emulsions According to Weight Percentages of Water Phase Parts and Oil Phase Parts According to compositions of Table 1, properties and states of the emulsions were confirmed after weighing fixed quantities of respective ingredients of the water phase parts, mixing and dissolving the weighed fixed quantities of the respective ingredients of the water phase parts using Agi mixer at 80° C. and 4,000 rpm for 60 minutes, slowly injecting separate dissolved oil phase parts into the mixed and dissolved water phase parts, and performing emulsification processes using Homo mixer at 80° C. and 4,000 rpm for 10 minutes to form emulsions.

TABLE 1

| | Ingredients | Example 1-1 | Example 1-2 | Example 1-3 | Example 1-4 | Example 1-5 |
|---|---|---|---|---|---|---|
| Water phase part | Polyvinyl alcohol | 10.00 | 6.00 | 4.00 | 2.00 | 0.50 |
| | Hyaluronic acid | 1.50 | 1.00 | 0.80 | 0.50 | 0.20 |
| | Carrageenan | 1.50 | 1.00 | 0.80 | 0.50 | 0.20 |
| | Polyethylene glycol (20) sorbitan stearate | 0.05 | 2.00 | 3.00 | 4.00 | 5.00 |
| | Glycerin | 10.00 | 8.00 | 5.00 | 3.00 | 0.50 |
| | Purified water | 76.85 | 62.00 | 36.40 | 20.00 | 8.60 |
| Oil phase part | Sorbitan stearate | 0.01 | 1.00 | 2.00 | 2.50 | 3.00 |
| | Dimethicone | 0.045 | 9.50 | 24.00 | 33.75 | 41.00 |
| | Hexyl laurate | 0.045 | 9.50 | 24.00 | 33.75 | 41.00 |
| Total | | 100.00 | 100.00 | 100.00 | 100.00 | 100.00 |

As represented in the foregoing Table 1, it is shown that oil phase parts of Example 1 according to the present invention have weight percentages of 0.1 to 85 wt % and can be all confirmed to form ivory white emulsions.

<Example 2> Confirming Whether or not to Form Oil-in-Water Type Emulsions According to Weight Percentages of Surfactants According to compositions of Table 2, properties and states of the emulsions were confirmed after weighing fixed quantities of respective ingredients of the water phase parts, mixing and dissolving the weighed fixed quantities of the respective ingredients of the water phase parts using Homo mixer at 80° C. and 4,000 rpm for 60 minutes, slowly injecting separate dissolved oil phase parts into the mixed and dissolved water phase parts, and performing emulsification processes using Homo mixer at 80° C. and 4,000 rpm for 10 minutes to form emulsions.

TABLE 2

| | Ingredients | Example 2-1 | Example 2-2 | Example 2-3 |
|---|---|---|---|---|
| Water phase part | Polyvinyl alcohol | 10.00 | 4.00 | 4.00 |
| | Hyaluronic acid | 1.50 | 0.80 | 0.80 |
| | Carrageenan | 1.50 | 0.80 | 0.80 |
| | Polyethylene glycol (20) sorbitan stearate | 0.04 | 10.00 | 20.00 |
| | Glycerin | 10.00 | 5.00 | 5.00 |
| | Purified water | 76.85 | 23.40 | 44.40 |
| Oil phase part | Sorbitan stearate | 0.01 | 5.00 | 10.00 |
| | Dimethicone | 0.05 | 25.50 | 7.50 |
| | Hexyl laurate | 0.05 | 25.50 | 7.50 |
| Total | | 100.00 | 100.00 | 100.00 |

As represented in the foregoing Table 2, it is shown that polyethylene glycol (20) sorbitan stearate and sorbitan stearate used as surfactants of Example 2 according to the present invention have weight percentages of 0.05 to 30 wt %, and can be all confirmed to form emulsions.

<Example 3> Confirming Whether or not to Form a Gel According to Irradiation Amounts of Gamma-Rays According to compositions of Table 3, it was confirmed whether a solid gel having fluidity was formed or not by containing the emulsion in a separate container and irradiating the gamma-rays to the emulsion with irradiation dose differences of 5 kGy, 15 kGy, 35 kGy and 50 kGy after weighing fixed quantities of respective ingredients of the water phase part, mixing and dissolving the weighed fixed quantities of the respective ingredients of the water phase part using Homo mixer at 80° C. and 4,000 rpm for 60 minutes, slowly injecting a separate dissolved oil phase part into the mixed and dissolved water phase part, and performing an emulsification process using Homo mixer at 80° C. and 4,000 rpm for 10 minutes to form an emulsion.

TABLE 3

| | Ingredients | Content (wt %) |
|---|---|---|
| Water phase part | Polyvinyl alcohol | 6.00 |
| | Hyaluronic acid | 1.00 |
| | Carrageenan | 1.00 |
| | Polyethylene glycol (20) sorbitan stearate | 3.00 |
| | Glycerin | 8.00 |
| | Purified water | 61.00 |
| Oil phase part | Sorbitan stearate | 1.00 |
| | Dimethicone | 9.50 |
| | Hexyl laurate | 9.50 |
| Total | | 100.0 |

TABLE 4

| Irradiation dose | Strength (kgf/cm$^2$) | Hardness (g/cm$^2$) |
|---|---|---|
| 5 kGy | 230.62 | 7,760.96 |
| 15 kGy | 370.75 | 10,107.36 |
| 35 kGy | 440.28 | 14,078.00 |
| 50 kGy | 511.12 | 18,647.40 |

As represented in confirmation of strength and hardness values of the gel according to irradiation amounts of gamma-rays of the foregoing Table 4, all solid gel forms having flexibility could be confirmed from the gel of Example 3 according to the present invention at a gamma-ray irradiation amount of 5 to 50 kGy, and it is shown that the more the irradiation amount is increased, the more strength and hardness values of the gel are increased.

<Example 4> Confirming Whether Gamma-Ray Irradiated Gels are Formed or not According to Weight Percentages of Polymers According to compositions of Table 5, it was confirmed whether solid gels having flexibility were formed or not by containing the emulsions in separate containers and irradiating the gamma-rays to the emulsions at an irradiation amount of 25 kGy/hr after weighing fixed quantities of respective ingredients of the water phase parts, mixing and dissolving the weighed fixed quantities of the respective ingredients of the water phase parts using Homo mixer at 80° C. and 4,000 rpm for 60 minutes, slowly injecting separate dissolved oil phase parts into the mixed and dissolved water phase parts, and performing emulsification processes using Homo mixer at 80° C. and 4,000 rpm for 10 minutes to form emulsions.

TABLE 5

| | Ingredients | Content (wt %) | | |
|---|---|---|---|---|
| | | Example 4-1 | Example 4-2 | Example 4-3 |
| Water phase part | Polyvinyl alcohol | 1.00 | 2.50 | 4.00 |
| | Hyaluronic acid | 0.25 | 0.50 | 1.00 |
| | Carrageenan | 0.25 | 0.50 | 1.00 |
| | Polyethylene glycol (20) sorbitan stearate | 4.00 | 4.00 | 4.00 |
| | Glycerin | 3.00 | 2.00 | 1.00 |
| | Purified water | 21.50 | 20.5 | 19.00 |
| Oil phase part | Sorbitan stearate | 2.50 | 2.50 | 2.50 |
| | Dimethicone | 33.75 | 33.75 | 33.75 |
| | Hexyl laurate | 33.75 | 33.75 | 33.75 |
| | Total | 100.00 | 100.00 | 100.00 |

As represented in the foregoing Table 5, solid gel forms which all have flexibility at a gamma-ray irradiation amount of 25 kGy when polyvinyl alcohol, hyaluronic acid and carrageenan used as polymers of Example 4 according to the present invention were contained in the water phase parts in amounts of 5 to 20 wt % based on the total weight percentages of the water phase parts could be confirmed.

<Example 5> Confirming Transparency Values According to Refractive Index Differences Between the Water Phase Parts and the Oil Phase Parts According to compositions of Table 6, transparency values of solid gels having flexibility were confirmed by containing the emulsions in separate containers, and irradiating the gamma-rays to the emulsions at an irradiation amount of 25 kGy/hr after weighing fixed quantities of respective ingredients of the water phase parts, mixing and dissolving the weighed fixed quantities of the respective ingredients of the water phase parts using Homo mixer at 80° C. and 4,000 rpm for 60 minutes, slowly injecting separate dissolved oil phase parts into the mixed and dissolved water phase parts, and performing emulsification processes using Homo mixer at 80° C. and 4,000 rpm for 10 minutes to form emulsions.

TABLE 6

| | Ingredients | Content (wt %) | |
|---|---|---|---|
| | | Example 5-1 | Example 5-2 |
| Water phase part | Polyvinyl alcohol | 6.00 | 6.00 |
| | Hyaluronic acid | 1.00 | 1.00 |
| | Carrageenan | 1.00 | 1.00 |
| | Polyethylene glycol (20) sorbitan stearate | 2.50 | 2.50 |
| | Glycerin | 37.20 | 24.80 |
| | Purified water | 32.30 | 44.70 |
| Oil phase part | Sorbitan stearate | 1.00 | 1.00 |
| | Dimethicone | 19.00 | 19.00 |
| | Hexyl laurate | 0.00 | 0.00 |
| | Octocrylene | 0.00 | 0.00 |
| | Total | 100.00 | 100.00 |

TABLE 7

| | Refractive index (25° C.) | |
|---|---|---|
| Items | Example 5-1 | Example 5-2 |
| Water phase part | 1.4043 | 1.3843 |
| Oil phase part | 1.4043 | 1.4043 |
| Refractive index difference | 0.0000 | 0.0200 |
| Transparency | 1 | 2 |

<1: Transparent, 2: Slightly opaque, 3: Opaque>

As shown in refractive indexes of the water phase parts and the oil phase parts of the foregoing Table 7, color changes from transparency to ivory white can be confirmed at refractive index differences of not more than 0.02 between the water phase parts and the oil phase parts of Example 5 according to the present invention.

<Example 6> Confirming Color Changes from Transparency to Ivory White According to Refractive Index Differences Between the Water Phase Parts and the Oil Phase Parts After cutting gels prepared according to compositions of Table 6 to a thickness of 2 mm, extents to which colors had been changed from transparency to ivory white were observed with the naked eye by attaching the cut gels to skins of 15 healthy adult men and women. After calculating average values of respective evaluation results, the calculated average values of the respective evaluation results are shown in the following Table 8.

TABLE 8

| | Extents of color change | | | | |
|---|---|---|---|---|---|
| Items | 5 minutes | 30 minutes | 60 minutes | 90 minutes | 120 minutes |
| Example 5-1 | ** | *** | **** | **** | **** |
| Example 5-2 | — | ** | ** | *** | *** |

<—: No change, *: Slight change, : Fair, *: Good, ****: Very good>

As represented in the foregoing Table 8, a color change from transparency to ivory white in case of Example 5-1 could be confirmed, and a color change in case of Example 5-2 could be confirmed although a variation range was not high starting from slightly opaque ivory white in the initial stage as results of confirming extents of color changes due to refractive index differences between the oil phase parts and the water phase parts when applying the oil phase parts and the water phase parts of Example 6 according to the present invention to the skin.

<Comparative Example 1> Confirming Oil-in-Water Type Emulsions According to Weight Percentages of Water Phase Parts and Oil Phase Parts According to compositions of Table 9, properties and states of the emulsions were confirmed after weighing fixed quantities of respective ingredients of the water phase parts, mixing and dissolving the weighed fixed quantities of the respective ingredients of the water phase parts using Agi mixer at 80° C. and 4,000 rpm for 60 minutes, slowly injecting separate dissolved oil phase parts into the mixed and dissolved water phase parts, and performing emulsification processes using Homo mixer at 80° C. and 4,000 rpm for 10 minutes to form emulsions.

TABLE 9

| | Ingredients | Comparative Example 1-1 | Comparative Example 1-2 | Comparative Example 1-3 | Comparative Example 1-4 |
|---|---|---|---|---|---|
| Water phase part | Polyvinyl alcohol | 10.00 | 10.00 | 2.00 | 1.00 |
| | Hyaluronic acid | 1.50 | 1.50 | 0.50 | 0.20 |
| | Carrageenan | 1.50 | 1.50 | 0.50 | 0.20 |
| | Polyethylene glycol (20) sorbitan stearate | 0.05 | 0.05 | 3.00 | 3.00 |
| | Glycerin | 10.00 | 10.00 | 1.00 | 1.00 |
| | Purified water | 76.92 | 76.90 | 5.00 | 2.60 |
| Oil phase part | Sorbitan stearate | 0.01 | 0.01 | 2.00 | 2.00 |
| | Dimethicone | 0.01 | 0.02 | 43.00 | 45.00 |
| | Hexyl laurate | 0.01 | 0.02 | 43.00 | 45.00 |
| | Total | 100.00 | 100.00 | 100.00 | 100.00 |

As represented in the foregoing Table 9, it is difficult to form ivory white emulsions when the oil phase part of Comparative Example 1 according to the present invention has a weight percentage of less than 0.10, and a water-in-oil type emulsion is not formed when the oil phase part of Comparative Example 1 according to the present invention has a weight percentage of 85 or more.

<Comparative Example 2> Confirming Whether or not to Form Oil-in-Water Type Emulsions According to Weight Percentages of Surfactants According to compositions of Table 10, properties and states of the emulsions were confirmed after weighing fixed quantities of respective ingredients of the water phase parts, mixing and dissolving the weighed fixed quantities of the respective ingredients of the water phase parts using Homo mixer at 80° C. and 4,000 rpm for 60 minutes, slowly injecting separate dissolved oil phase parts into the mixed and dissolved water phase parts, and performing emulsification processes using Homo mixer at 80° C. and 4,000 rpm for 10 minutes to form emulsions.

TABLE 10

| | Ingredients | Comparative Example 2-1 | Comparative Example 2-2 |
|---|---|---|---|
| Water phase part | Polyvinyl alcohol | 10.00 | 4.00 |
| | Hyaluronic acid | 1.50 | 0.80 |
| | Carrageenan | 1.50 | 0.80 |
| | Polyethylene glycol (20) sorbitan stearate | 0.03 | 23.00 |
| | Glycerin | 10.00 | 5.00 |
| | Purified water | 76.86 | 41.40 |
| Oil phase part | Sorbitan stearate | 0.01 | 12.00 |
| | Dimethicone | 0.045 | 6.50 |
| | Hexyl laurate | 0.045 | 6.50 |
| | Total | 100.00 | 100.00 |

As represented in the foregoing Table 10, polyethylene glycol (20) sorbitan stearate and sorbitan stearate used as surfactants of Example 2 according to the present invention are not suitable for the present invention since a phenomenon that oil floats on emulsions when polyethylene glycol (20) sorbitan stearate and sorbitan stearate are contained in a weight percentage of 0.05 or less, and translucent emulsions are formed when polyethylene glycol (20) sorbitan stearate and sorbitan stearate are contained in a weight percentage of 30 or more.

<Comparative Example 3> Confirming Whether or not to Form a Gel According to Irradiation Amounts of Gamma-Rays According to compositions of Table 3, it was confirmed whether a solid gel having fluidity was formed or not by containing the emulsion in a separate container and irradiating the gamma-rays to the emulsion in different irradiation doses after weighing fixed quantities of respective ingredients of the water phase part, mixing and dissolving the weighed fixed quantities of the respective ingredients of the water phase part using Homo mixer at 80° C. and 4,000 rpm for 60 minutes, slowly injecting a separate dissolved oil phase part into the mixed and dissolved water phase part, and performing an emulsification process using Homo mixer at 80° C. and 4,000 rpm for 10 minutes to form an emulsion.

TABLE 11

| Irradiation dose | Strength (kgf/cm$^2$) | Hardness (g/cm$^2$) |
|---|---|---|
| 2 kGy | 80.67 | 2,711.40 |
| 80 kGy | 887.78 | 31,471.61 |

As represented in confirmation of strength and hardness values of the gel according to irradiation amounts of gamma-rays of the foregoing Table 11, it is difficult to see the gel as a solid form of the present research since the gel of Example 3 according to the present invention has a very low strength at a gamma-ray irradiation amount of 2 kGy, and the gel of Example 3 according to the present invention does not have flexibility of the present research since a phenomenon that the gel having all solid forms is easily broken without having flexibility is confirmed at a gamma-ray irradiation amount of 80 kGy.

<Comparative Example 4> Confirming Whether Gamma-Ray Irradiated Gels are Formed or not According to Weight Percentages of Polymers According to compositions of Table 12, it was confirmed whether solid gels having flexibility were formed or not by containing the emulsions in separate containers and irradiating the gamma-rays to the emulsions at an irradiation amount of 25 kGy/hr after weighing fixed quantities of respective ingredients of the water phase parts, mixing and dissolving the weighed fixed quantities of the respective ingredients of the water phase parts using Homo mixer at 80° C. and 4,000 rpm for 60 minutes, slowly injecting separate dissolved oil phase parts into the mixed and dissolved water phase parts, and performing emulsification processes using Homo mixer at 80° C. and 4,000 rpm for 10 minutes to form emulsions.

TABLE 12

| | Ingredients | Content (wt %) | |
|---|---|---|---|
| | | Comparative Example 4-1 | Comparative Example 4-2 |
| Water phase part | Polyvinyl alcohol | 0.40 | 5.00 |
| | Hyaluronic acid | 0.25 | 1.00 |
| | Carrageenan | 0.25 | 1.50 |
| | Polyethylene glycol (20) sorbitan stearate | 4.00 | 4.00 |
| | Glycerin | 3.00 | 1.00 |
| | Purified water | 22.10 | 17.50 |
| Oil phase part | Sorbitan stearate | 2.50 | 2.50 |
| | Dimethicone | 33.75 | 33.75 |
| | Hexyl laurate | 33.75 | 33.75 |
| | Total | 100.00 | 100.00 |

As represented in the foregoing Table 12, it is difficult to see the solid gels as a solid gel of the present invention since the solid gels are formed in such a form that is extended at a gamma-ray irradiation amount of 25 kGy when polyvinyl alcohol, hyaluronic acid and carrageenan used as polymers of Comparative Example 4 according to the present invention were contained in the water phase parts in amounts of 3 wt % based on the total weight percentages of the water phase parts, and it is difficult for the solid gels to have flexibility since flowability is dropped due to a high viscosity, and strength values of the gels are too high at the gamma-ray irradiation amount of 25 kGy when the polymers were contained in the water phase parts in amounts of 25 wt % based on the total weight percentages of the water phase parts.

<Comparative Example 5> Confirming Transparency Values According to Refractive Index Differences Between the Water Phase Parts and the Oil Phase Parts According to compositions of Table 13, transparency values of solid gels having flexibility were confirmed by containing the emulsions in separate containers, and irradiating the gamma-rays to the emulsions at an irradiation amount of 25 kGy/hr after weighing fixed quantities of respective ingredients of the water phase parts, mixing and dissolving the weighed fixed quantities of the respective ingredients of the water phase parts using Homo mixer at 80° C. and 4,000 rpm for 60 minutes, slowly injecting separate dissolved oil phase parts into the mixed and dissolved water phase parts, and performing emulsification processes using Homo mixer at 80° C. and 4,000 rpm for 10 minutes to form emulsions.

TABLE 13

| | Ingredients | Content (wt %) | | |
|---|---|---|---|---|
| | | Comparative Example 5-1 | Comparative Example 5-2 | Comparative Example 5-3 |
| Water phase part | Polyvinyl alcohol | 6.00 | 6.00 | 6.00 |
| | Hyaluronic acid | 1.00 | 1.00 | 1.00 |
| | Carrageenan | 1.00 | 1.00 | 1.00 |
| | Polyethylene glycol (20) sorbitan stearate | 2.50 | 2.50 | 2.50 |
| | Glycerin | 0.00 | 0.00 | 0.00 |
| | Purified water | 69.5 | 69.5 | 69.5 |
| Oil phase part | Sorbitan stearate | 1.00 | 1.00 | 1.00 |
| | Dimethicone | 16.86 | 9.07 | 0.00 |
| | Hexyl laurate | 2.14 | 9.93 | 2.69 |
| | Octocrylene | 0.00 | 0.00 | 16.31 |
| | Total | 100.00 | 100.00 | 100.00 |

TABLE 14

| | Refractive index (25° C.) | | |
|---|---|---|---|
| Items | Comparative Example 5-1 | Comparative Example 5-2 | Comparative Example 5-3 |
| Water phase part | 1.3425 | 1.3425 | 1.3425 |
| Oil phase part | 1.4125 | 1.4425 | 1.5425 |
| Refractive index difference | 0.0700 | 0.1000 | 0.2000 |
| Transparency | 3 | 3 | 3 |

<1: Transparent, 2: Slightly opaque, 3: Opaque>

As shown in refractive indexes of the water phase parts and the oil phase parts of the foregoing Table 14, color changes from transparency to ivory white cannot be confirmed since opacity can be confirmed at refractive index differences of 0.07 or more between the oil phase parts and the water phase parts of Comparative Example 5 according to the present invention.

<Comparative Example 6> Confirming Color Changes from Transparency to Ivory White According to Refractive Index Differences Between the Water Phase Parts and the Oil Phase Parts After cutting gels prepared according to compositions of Table 13 to a thickness of 2 mm, extents to which colors had been changed from transparency to ivory white were observed with the naked eye by attaching the cut gels to skins of 15 healthy adult men and women. After calculating average values of respective evaluation results, the calculated average values of the respective evaluation results are shown in the following Table 15.

TABLE 15

| | Extents of color change | | | | |
|---|---|---|---|---|---|
| Items | 5 minutes | 30 minutes | 60 minutes | 90 minutes | 120 minutes |
| Comparative Example 5-1 | — | — | — | — | — |
| Comparative Example 5-2 | — | — | — | — | — |
| Comparative Example 5-3 | — | — | — | — | — |

<—: No change, *: Slight change, : Fair, *: Good, ****: Very good>

As represented in the foregoing Table 15, color changes from transparency to ivory white have not been occurred autonomously in Comparative Examples 5-1, 5-2 and 5-3 as results of confirming extents of color changes due to refractive index differences between the oil phase parts and the water phase parts when applying the oil phase parts and the water phase parts of Comparative Example 6 according to the present invention to the skin.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A solid temporal colorimetric hydrogel cosmetic composition having flexibility by irradiation of gamma-rays which is an oil-in-water type hydrogel cosmetic composition comprising
a water phase part and an oil phase part,
wherein the cosmetic composition comprises 15 to 99.90 wt % of the water phase part and 0.10 to 85 wt % of the oil phase part based on the total weight percentage of the composition,
wherein the water phase part comprises a polymer, a refractive index regulator, and purified water, and the water phase part comprises 3.0 to 30 wt % of the polymer and 3 to 60 wt % of the refractive index regulator based on the total weight percentage of the water phase part,
wherein the water phase part and the oil phase part have a refractive index difference of 0 to 0.02 therebetween, the cosmetic composition has 5 to 50 kGy gamma-rays irradiated thereto, resulting in solid gel formation and having flexibility, and
the cosmetic composition further comprises a color change according to variations in a refractive index difference between the water phase part and the oil phase part by absorption of moisture and volatiles when applying the cosmetic composition to the skin.

2. The solid temporal colorimetric hydrogel cosmetic composition of claim 1, wherein the polymer is a zwitterionic polymer, a cationic polymer, an anionic polymer, or a nonionic polymer.

3. The solid temporal colorimetric hydrogel cosmetic composition of claim 1, wherein the polymer is at least one member selected from the group of hyaluronic acid, hyaluronic acid salts, carrageenan, polyvinyl alcohol, and polyvinyl pyrrolidone.

4. The solid temporal colorimetric hydrogel cosmetic composition of claim 1, wherein the refractive index regulator is at least one member selected from the group of polyhydric alcohols, saccharide, polyoxyalkylene, polyoxyalkylene copolymer, polyoxyalkylene-containing alcohols, and silicone/polyalkylene copolymer.

5. The solid temporal colorimetric hydrogel cosmetic composition of claim 1, wherein the water phase part and the oil phase part include a surfactant.

6. The solid temporal colorimetric hydrogel cosmetic composition of claim 5, wherein the cosmetic composition comprises 0.05 to 30 wt % of the surfactant based on the total weight percentage of the composition.

7. The solid temporal colorimetric hydrogel cosmetic composition of claim 5, wherein the surfactant is an anionic surfactant, a cationic surfactant, a nonionic surfactant, or an amphoteric surfactant.

8. The solid temporal colorimetric hydrogel cosmetic composition of claim 1, wherein the oil phase part includes a refractive index regulator and oil.

9. The solid temporal colorimetric hydrogel cosmetic composition of claim 8, wherein the oil is at least one member selected from the group including a silicon-based oil, a hydrocarbon oil, an ester-based oil, a natural oil, a higher alcohol, and a fatty acid.

10. The solid temporal colorimetric hydrogel cosmetic composition of claim 8, wherein the refractive index regulator of the oil phase part is any one of ingredients composing the oil phase part by including oil.

11. A method of preparing a solid temporal colorimetric hydrogel cosmetic composition having flexibility by irradiation of gamma-rays, as a method of preparing an oil-in-water type hydrogel cosmetic composition comprising a water phase part and an oil phase part, the method comprising the steps of:
a step (S1) of mixing and dissolving respective ingredients of the water phase part;
a step (S2) of mixing and dissolving respective ingredients of the oil phase part;
a step (S3) of forming an emulsion by emulsifying a mixed and dissolved water phase part into a mixed and dissolved oil phase part;
a step (S4) of irradiating the gamma-rays to the emulsion; and
a step (S5) of confirming whether a solid gel having fluidity is formed or not,
wherein the cosmetic composition comprises 15 to 99.90 wt % of the water phase part and 0.10 to 85 wt % of the oil phase part based on the total weight percentage of the composition,
wherein the water phase part comprises a polymer, a refractive index regulator, and purified water, and the water phase part comprises 3.0 to 30 wt % of the polymer and 3 to 60 wt % of the refractive index regulator based on the total weight percentage of the water phase part,
wherein the water phase part and the oil phase part have a refractive index difference of 0 to 0.02 therebetween, the cosmetic composition has 5 to 50 kGy gamma-rays irradiated thereto, resulting in solid gel formation and having flexibility, and the cosmetic composition comprises a color change according to variations in a refractive index difference between the water phase part and the oil phase part by absorption of moisture and volatiles when applying the cosmetic composition to the skin.

12. The method of claim 11, wherein the step (S1) comprises mixing and dissolving respective ingredients of the water phase part at 60 to 85° C. and 4,000 rpm for 50 to 70 minutes.

13. The method of claim 11, wherein the step (S3) comprises injecting the mixed and dissolved oil phase part into the mixed and dissolved water phase part, and performing an emulsification process at 60 to 85° C. and 4,000 rpm for 8 to 20 minutes to form am emulsion.

14. A solid temporal colorimetric hydrogel cosmetic composition having flexibility by irradiation of gamma-rays which is an oil-in-water type hydrogel cosmetic composition comprising a water phase part and an oil phase part,
wherein the cosmetic composition comprises 15 to 99.90 wt % of the water phase part and 0.10 to 85 wt % of the oil phase part based on the total weight percentage of the composition,
wherein the water phase part comprises a polymer, a refractive index regulator, and purified water, and the water phase part comprises 3.0 to 30 wt % of the polymer and 3 to 60 wt % of the refractive index regulator based on the total weight percentage of the water phase part, wherein the oil phase part comprises a refractive index regulator and oil, wherein the water phase part and the oil phase part have a refractive index difference of 0 to 0.02 therebetween, the cosmetic composition has 5 to 50 kGy gamma-rays irradiated thereto, resulting in solid gel formation and having flexibility, and the cosmetic composition further comprises a color change according to variations in a refractive index difference between the water phase part and the oil phase part by absorption of moisture and volatiles when applying the cosmetic composition to a skin.

* * * * *